United States Patent [19]

Woltersdorf, Jr. et al.

[11] Patent Number: 4,797,391

[45] Date of Patent: Jan. 10, 1989

[54] ((5,6-DICHLORO-3-OXO-9,9A-DISUBSTITUTED-2,3,9,9A-TETRAHYDROFLUOREN-7-YL)OXY)ALKANOIC ACIDS AND ALKANIMIDAMIDES

[75] Inventors: Otto W. Woltersdorf, Jr., Chalfont; Edward J. Cragoe, Jr., Lansdale; Adolph M. Pietruszkiewicz, North Wales, all of Pa.

[73] Assignee: Merck & Co., Inc., Rahway, N.J.

[21] Appl. No.: 150,462

[22] Filed: Feb. 8, 1988

Related U.S. Application Data

[63] Continuation of Ser. No. 910,924, Sep. 24, 1986, abandoned.

[51] Int. Cl.$^4$ .................. A61K 31/645; C07C 129/12
[52] U.S. Cl. ..................... 514/120; 514/121; 514/125; 514/510; 514/567; 514/569; 558/195; 560/45; 560/53; 562/452; 564/246; 564/247
[58] Field of Search ................. 564/246, 247; 560/45, 560/53; 558/195; 562/452; 514/567, 569, 637, 120, 121, 125, 510

[56] References Cited

U.S. PATENT DOCUMENTS

| | | | |
|---|---|---|---|
| 4,316,043 | 2/1982 | Cragoe et al. | 562/461 |
| 4,317,922 | 3/1982 | Cragoe, Jr. et al. | 562/461 |
| 4,337,354 | 6/1982 | Cragoe, Jr. et al. | 562/461 |
| 4,356,313 | 10/1982 | Cragoe, Jr. et al. | 580/53 |
| 4,356,314 | 10/1982 | Cragoe, Jr. et al. | 560/53 |
| 4,389,417 | 6/1983 | Bourke et al. | 514/577 |
| 4,394,385 | 7/1983 | Cragoe, Jr. | 514/444 |
| 4,463,208 | 7/1984 | Cragoe, Jr. et al. | 562/462 |
| 4,465,850 | 8/1984 | Cragoe, Jr. et al. | 560/53 |
| 4,579,869 | 4/1986 | Cragoe, Jr. et al. | 514/561 |
| 4,604,396 | 8/1986 | Cragoe et al. | 564/247 |

OTHER PUBLICATIONS

J. Med. Chem. (1982) Cragoe, et al. 25 pp. 567–679.
J. Med. Chem. (1986) Cragoe, et al. 29 pp. 825–842.

Primary Examiner—Donald B. Moyer
Assistant Examiner—Bruce D. Gray
Attorney, Agent, or Firm—Hesna J. Pfeiffer; Charles M. Caruso

[57] ABSTRACT

The invention relates to novel [(5,6-dichloro-3-oxo-9,9a-disubstituted-2,3,9,9a-tetrahydro-fluoren-7-yl)oxy]alkanoic acids and alkanimidamides, their derivatives and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections, various brain concussions and elevated intracranial pressure.

16 Claims, No Drawings

((5,6-DICHLORO-3-OXO-9,9A-DISUBSTITUTED-2,3,9,9A-TETRAHYDROFLUOREN-7-YL)OXY)ALKANOIC ACIDS AND ALKANIMIDAMIDES

This is a continuation, of application Ser. No. 910,924, filed 9/24/86, now abandoned.

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections, various concussions and elevated intracranial pressure results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

Two recent publications, one entitled "*Agents for the Treatment of Brain Injury*" 1. (Aryloxy)alkanoic Acids, by Cragoe et al, J. Med. Chem., (1982) 25, 567–579 and the other, "Agents for the Treatment of Brain Edema" 2. "[(2,3,9,9a-tetrahydro-3-oxo-9a-subtituted-1H-fluoren-7-yl)oxy]alkanoic Acids and Their Analogs", by Cragoe et al, Med. Chem., 29, 825–841 (1986), report recent experimental testing of agents for treatment of brain injury and review the current status of treatment of brain injury. Additionally, U.S. Pat. Nos. 4,316,043, 4,317,922, 4,337,354, 4,356,313, 4,356,314, 4,389,417, 4,394,385, 4,463,208, 4,465,850, 4,579,869, and 4,604,396 disclose certain alkanoic acids, cycloalkanoic acids or their amidine analogs for the treatment of grey matter edema.

The compounds of the invention have the added advantage of being devoid of the pharmacodynamic, toxic or various side effects characteristic of the diuretics, steroids and barbiturates.

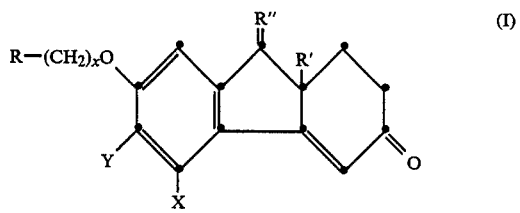

wherein:
R is

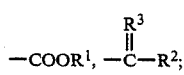

R' is lower alkyl, branched or unbranched, containing from 1 to 5 carbon atoms such as methyl, ethyl, n-propyl, isopropyl and the like, aryl such as phenyl, halo substituted aryl such as p-fluorophenyl, o-fluorophenyl, p-chlorophenyl and the like, aralkyl such as benzyl, cycloalkyl containing from 3 to 6 nuclear carbon atoms such as cyclopropyl, cyclobutyl, cyclopentyl and the like, or cycloalkyl-lower alkyl containing from 4 to 7 total carbon atoms such as cyclopentylmethyl and the like;

R" is =O, or H plus

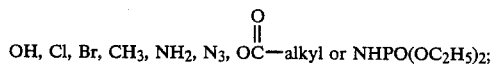

$R^1$ is hydrogen, $C_1$-$C_6$ alkyl, $C_1$-$C_6$ carboxyalkyl such as 1-carboxy-1-methylethyl;

$R^2$ is $NH_2$, $NHR^4$ or $NR^4R^5$;

$R^3$ is NH or $NR^4$;

$R^4$, $R^5$ are each independently lower alkyl, branched or unbranched, containing from 1 to 5 carbon atoms, or amino, provided that $R^4$ and $R^5$ are not both amino;

wherein $R^2$ and $R^3$ may be joined together via $R^4$ to form a heterocyclic ring of 5 or 6 atoms containing 2 nitrogen atoms and 3 or 4 carbon atoms, such as:

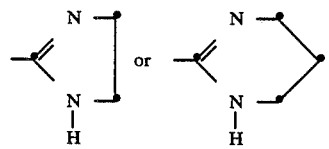

or wherein $R^4$ and $R^5$ may be joined together to form a 5- or 6-membered ring containing one nitrogen atom and 4 or 5 carbon atoms, such as:

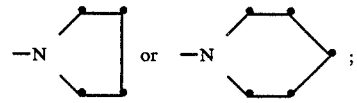

X and Y are halo or lower alkyl, such as methyl; and x is 1 to 4.

When R" is =O, the 9a-carbon atom in the molecule is asymmetric, the compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

When R" is other than =O, both the 9 and the 9a-carbon atoms are asymmetric, thus these compounds consist of two diasteriomers which can be separated by physical methods. Then, each diasteriomer which are racemic can be separated by classic resolution methods to the component enantiomers. This invention includes pure diasteriomers, the racemates and the pure enantiomers.

Since the alkanimidamide products of the invention are basic, the invention also includes the obvious pharmaceutically acceptable acid addition salts such as the hydrochloride, hydrobromide, sulfate, isethionate, acetate, methanesulfonate, maleate, succinate and the like salts.

Likewise, since the alkanoic acid products of the invention are acidic, the invention also includes the obvious pharmaceutically acceptable salts such as the sodium, potassium, ammonium, trimethylammonium, piperazinium, 1-methylpiperazinium, guanidinium, bis-(2-hydroxyethyl)ammonium, N-methylglucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel [(5,6-dichloro-3-oxo-9,9a-disubstituted-2,3,9,9a-tetrahydrofluoren-7-yl)oxy]alkanoic acids and alkanimidamides, and their salts, it also includes their derivatives, such as the esters, amides, oximes, hydrazones and the like. Additionally, this invention includes pharmaceutical compositions in unit dosage form containing a pharmaceutical carrier and an effective amount of a compound of Formula I, its R or S enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II

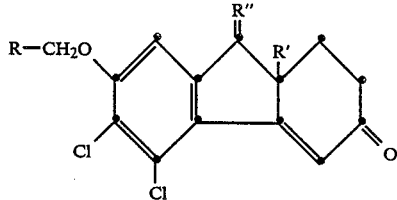

wherein:

R is carboxy,

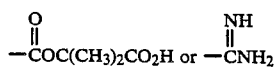

R' is lower alkyl, branched or unbranched, containing from 1 to 5 carbon atoms; and R'' is =O, H plus

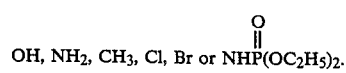

Also included are each diasteriomer (where they exist) and the enantiomers of each racemate.

A preferred compound is [(5,6-dichloro-3,9-dioxo-9a-propyl-2,3,9,9a-tetrahydro-1H-fluoren-7-yl)oxy]acetic acid.

Also preferred is 1-carboxy-1-methylethyl [(5,6-dichloro-3,9-dioxo-9a-propyl-2,3,9,9a-tetrahydro-1H-fluoren-7-yl)oxy]acetate.

Also preferred is [(5,6-dichloro-9-hydroxy-3-oxo-9a(-R+)-propyl-2,3,9,9a-tetrahydro-1H-fluoren-7-yl)oxy]acetic acid.

Also preferred is [(5,6-dichloro-9a-ethyl-9-methyl-3-oxo-2,3,9,9a-tetrahydro-1H-fluoren-7-yl)oxy]acetic acid.

Also preferred is ethyl [(9-amino-5,6-dichloro-3-oxo-9a(R)-propyl-2,3,9,9a-tetrahydro-1H-fluoren-7-yl)oxy]acetate hydrochloride.

Also preferred is [(3-oxo-9a(R)-propyl-2,3,9,9a-tetrahydro-5,6,9-trichloro-1H-fluoren-7-yl)oxy]acetic acid.

Also preferred is {[(5,6-dichloro-9-(diethoxyphosphoramido)-3-oxo-9a(R)-propyl-2,3,9,9a-tetrahydro-1H-fluoren-7-yl]oxy}acetic acid.

Also preferred is 2-[(5,6-dichloro-3,9-dioxo-9a-propyl-2,3,9,9a-tetrahydro-1H-fluoren-7-yl)oxy]ethanimidamide hydrochloride.

Especially preferred are the pure diasteriomers and pure enantiomers since, in most instances, one diasteriomer or one enantiomer is more active biologically than the other.

Included within the scope of this invention are the pharmaceutically acceptable salts of [(5,6-dichloro-3-oxo-9,9a-disubstituted-2,3,9,9a-tetrahydro-fluoren-7-yl)oxy]alkanoic acids and alkanimidamides since a major medical use of these compounds is solutions of their soluble salts which can be administered parenterally.

Thus, the acid addition salts can be prepared by the reaction of the [(5,6-dichloro-3-oxo-9,9a-disubstituted-2,3,9,9a-tetrahydrofluoren-7-yl)oxy]alkanoic acids of this invention with an appropriate alkali metal hydroxide, carbonate or bicarbonate such as sodium hydroxide, potassium hydroxide, sodium carbonate, sodium bicarbonate and the like or an organic base, such as ammonium hydroxide, piperazine, 1-methyl-piperazine, guanidine, bis-(2-hydroxyethyl)amine, N-methylglucosamine and the like. Salts of the alkanimidamides of this invention may be prepared by reaction of the free bases with an appropriate pharmaceutically acceptable mineral acid or organic carboxylic acid, such as hydrochloric acid, sulfuric acid, hydrobromic acid, isethionic acid, methanesulfonic acid, maleic acid, succinic acid, acetic acid and the like. The salts selected are derived from among the non-toxic, pharmaceutically acceptable acids. Alternatively, the nature of these salts can be determined by the amine salt selected in their synthesis.

The synthesis of the compounds of this invention in which R'' is =O (Ia) is accomplished as illustrated by the following five-step series of reactions to produce Compound VIII.

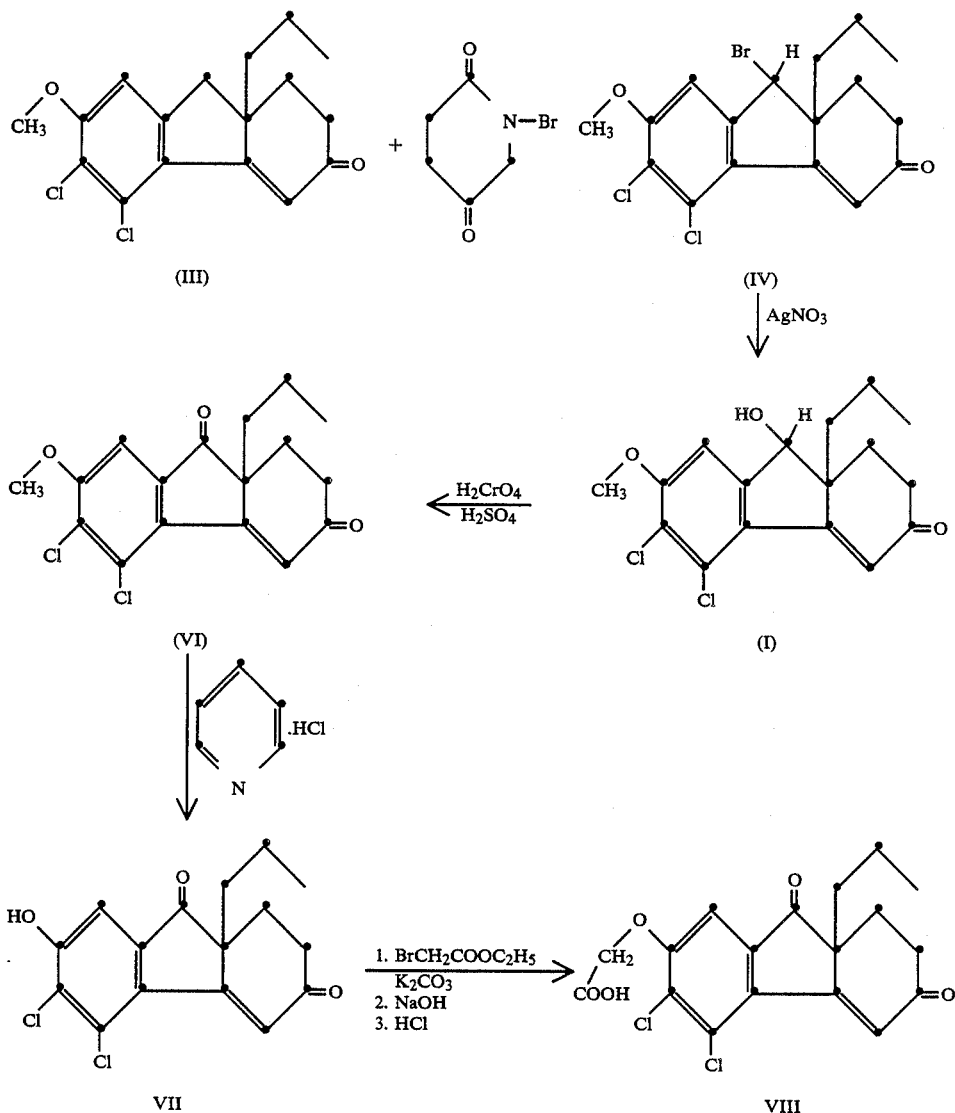

A compound of Formula III is reacted wth N-bromosuccinimide in a solvent such as CCl₄ or CHCl₃ and catalysed by a peroxide such as benzoyl peroxide at a temperature of from 50° C. to the reflux temperature of the solvent. The resultant compound of Formula IV is reacted with silver nitrate in an alcohol, such as 2-methoxyethanol containing water at a temperature of from 50° C. to the reflux temperature of the solvent to give a keto-alcohol of Formula V which is oxidized to a diketone of Formula VI by an oxidizing agent such as chromic acid (Jones reagent), pyridinium chromate, potassium permanganate and the like. The ether function of Formula VI is cleaved in molten pyridine hydrochloride to a compound of Formula VII which is alkylated with ethyl bromoacetate and the resultant ester hydrolysed to give the compound of Formula VIII. Other compounds of this invention of the type illustrated by Formula VIII may be prepared in a fashion similar to that described for this compound.

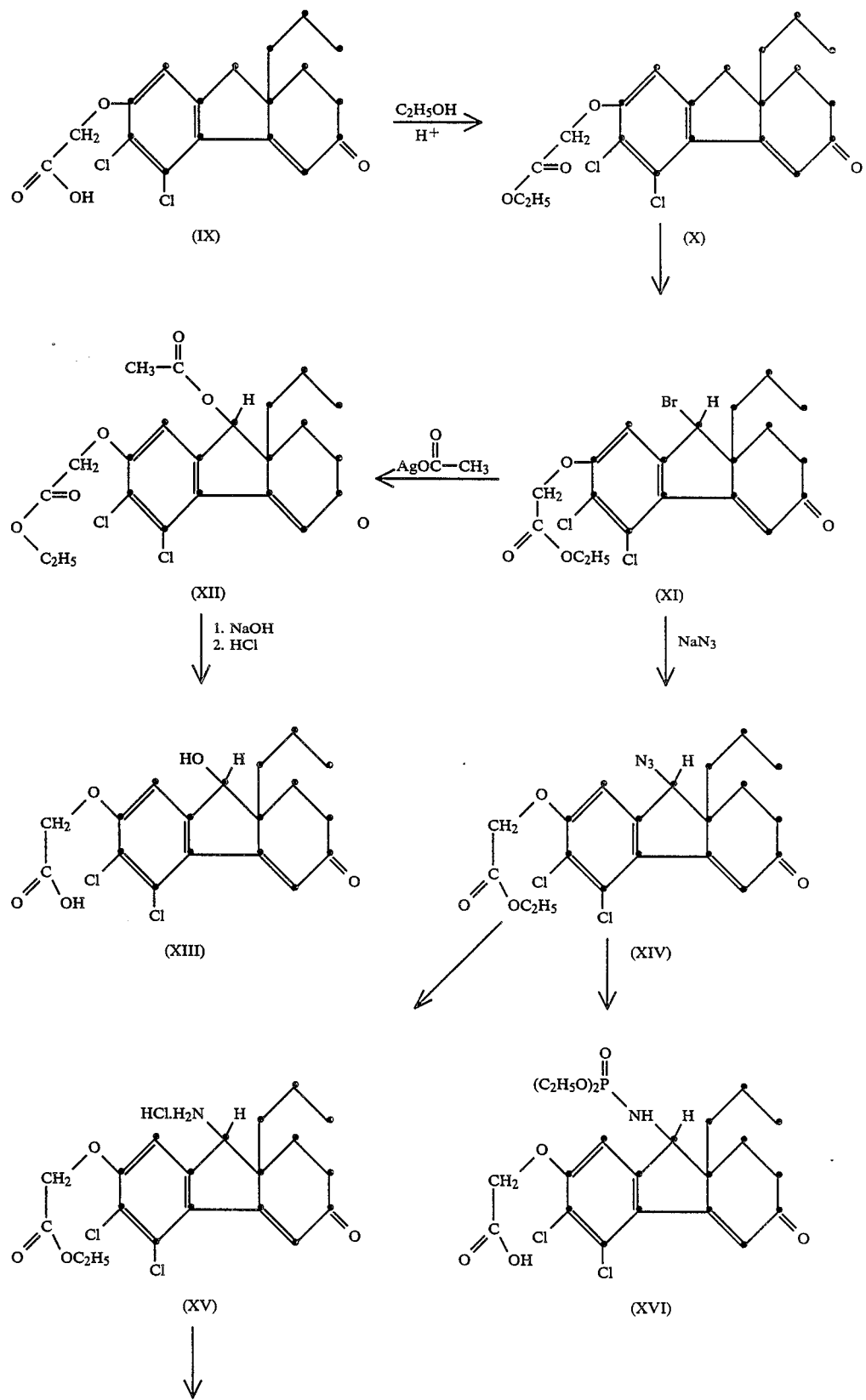

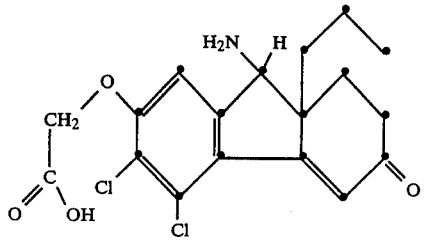

(XVa)

The compounds of this invention wherein R' is H plus Br (or Cl), OCOCH₃, OH, N₃, NH₂, NHPO(OC₂H₅)₂ can be prepared by the methods illustrated for the synthesis of compounds of Formula XI, XII, XIII, XIV, XV and XVI.

Ester X can be prepared by the classic esterification reaction of carboxylic acid IX using refluxing ethanol in the presence of an acid catalyst such as sulfuric acid for a period of 1 to 4 hours. The 9-bromo compound of Formula XI is prepared by refluxing a solution of Compound X and N-bromosuccinimide in carbon tetrachloride containing a catalytic amount of a peroxide, such as benzoyl peroxide or p-chlorobenzoyl peroxide for a period of 1 to 3 hours.

The corresponding 9-chloro compound (XIa) can be prepared by substituting N-chlorosuccinimide for the N-bromosuccinimide in the reaction with compound X. The synthesis of the carboxylic acids corresponding to compounds XI or XIa can be accomplished by reacting compound IX with N-bromosuccinimide or N-chlorosuccinimide.

Alternatively, the carboxylic acids corresponding to XI or XIa can be prepared by saponification of the esters (XI and XIa) using an aqueous alcoholic solution of base, such as sodium or potassium hydroxide at a temperature of 15° to 25° C. for a period of 1 to 12 hours. Upon acidification of the solution with an acid, such as hydrochloric acid, the carboxylic acids, [(9-bromo-5,6-dichloro-3-oxo-9a(R)-propyl-2,3,9,9a-tetrahydro-1H-fluoren-7-yl)oxy]acetic acid and [(3-oxo-9a(R)-propyl-2,3,9,9a-tetrahydro-5,6,9-trichloro-1H-fluoren-7-yl)oxy]acetic acid is produced.

Compound XI is converted to the corresponding 9-acetoxy derivative (XII) by heating with silver acetate in a mixture of acetic acid and water for a period of 2 to 5 hours at a temperature of 75° to 110° C. Compound XIII is prepared by heating Compound XII in aqueous methanolic sodium hydroxide at 15°–40° C. for 2 to 6 hours followed by acidification.

Compound XI is converted to the azide (XIV) by reaction with sodium azide in a solvent or solvents, i.e., benzene, N,N-dimethylformamide and the like in the presence of a tetraalkylammonium halide, such as tetrabutylammonium bromide, preferably at the reflux temperature of the solvent or solvents or solvent mixture. Reduction of Compound XIV to the corresponding amine (XV) is accomplished with triphenylphosphine in a solvent mixture, such as tetrahydrofuran and water. The free acid corresponding to Compound XV, i.e. XVa, is prepared by saponification of XV in aqueous alcoholic alkali, followed by acidification. Reaction of Compound XIV with a trialkylphosphate at a temperature of 0° to 50° C. in a solvent, such as benzene, toluene and the like gives the phosphoramide, i.e. Compound XVI.

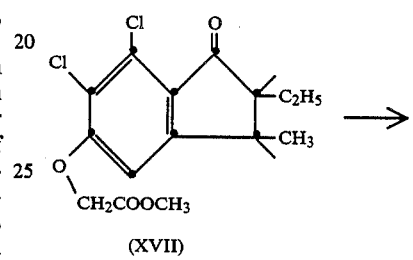

(XVII)

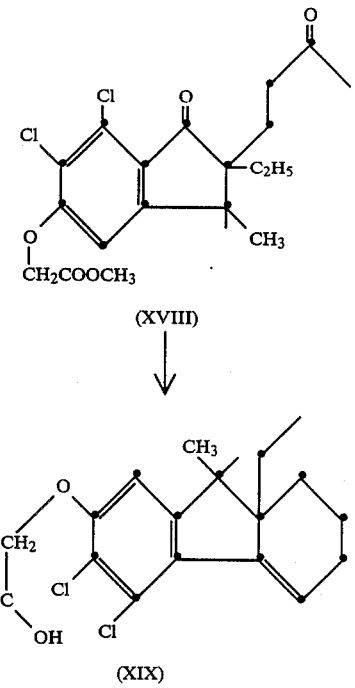

The compounds of Formula I where R″=H plus CH₃ can be prepared by the method illustrated by the 3-step synthesis of Compound XIX from Compound XVII.

Treatment of Compound XVII with methyl vinyl ketone in tetrahydrofuran by heating at 50° to 60° in the presence of a catalyst, such as 1,5-diazabicyclo[4.3.0]-non-5-ene (DBN) or 1,8-diazabicyclo-[5.4.0]undec-7-ene (DBU) gives the diketone of Formula XVIII. The Robinson annulation of Compound XVIII and simultaneous hydrolysis to give Compound XIX is accomplished by heating at a temperature of 80° C. to 105° C.

for a period of 60 to 100 hours in a solution of acetic acid and aqueous hydrochloric acid.

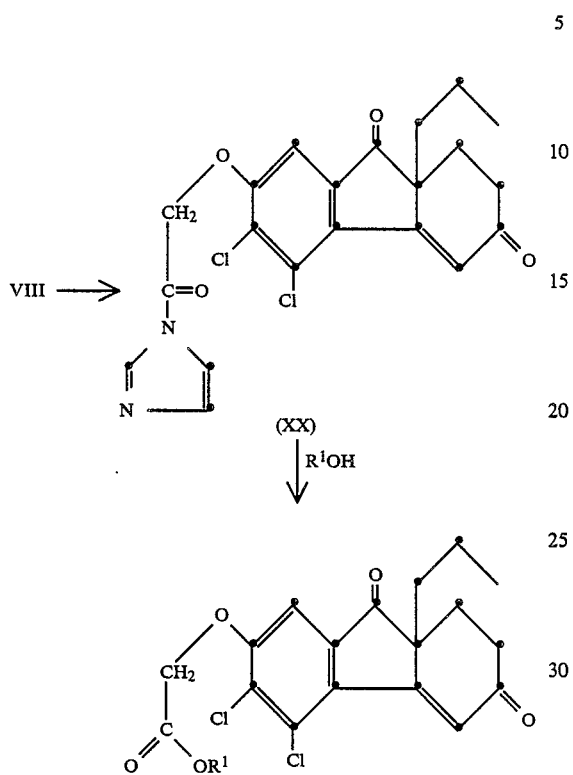

Esters of Formula I wherein $R=COOR^1$ are prepared by the two-step synthesis illustrated for the preparation of the compound of Formula XXI from Compound VIII. Reaction of Compound VIII with 1,1-carbonyldiimidazole in a solvent like tetrahydrofuran or N,N-dimethylformamide at a temperature of 15° to 30° C. for a period of 15 minutes to 5 hours gives the acylimidazole XX. Reaction of Compound XX with an alcohol of Formula R'OH is carried out in the same reaction milieu in which Compound VII was produced. The reaction is conducted at a temperature of 15° to 50° C. for a period of 10 to 24 hours. By reacting Compound XX with ammonia or a primary or secondary amine, the amide or substituted amide corresponding to Compound VIII is produced.

The alkanimidamides of Formula I can be produced by either of two methods. The first method is illustrated by the two-step synthesis of Compound XXIII from Compound VII.

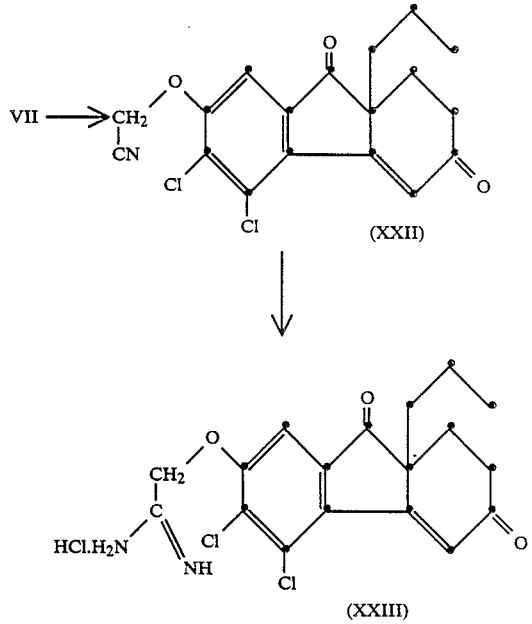

Phenol VII is treated with chlroacetonitrile in the presence of potassium carbonate in a solvent like N,N-dimethylformamide to give nitrile XXII. The reaction is conducted at 40° to 75° C. for a period of 15 minutes to two hours. Treatment of Compound XXII with methanol containing a catalytic amount of sodium methoxide produces the corresponding imido ester. The reaction occurs at a temperature of 15° to 30° C. during a period of 35 minutes to 3 hours and is generally conducted in an inert atmosphere, i.e., dry nitrogen or argon. The imido ester is reacted with ammonium chloride in the same milieu for 1½ to 4 hours at 20°–40° C. By using another amine or hydrazine salt alkanimidamides of Formula I where

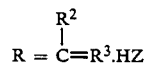

are obtained where Z is an organic or inorganic anion.

The phenols of Formula VII are qenerally racemic, however, the pure enantiomers (VIIa) can be made by the reaction of the pure carboxylic acids of Formula Ia with molten pyridine hydrochloride at 180° to 190° for a period of 15 minutes to 30 minutes. The compound of Formula Ia is resolved by the classic methods to be described later. Thus, by using the pure enantiomer of phenol VIIa, the corresponding pure enantiomer of the nitrile (XXIIa) is obtained which, in turn is converted to the pure enantiomer of the alkanimidamide salt (XXIIIa):

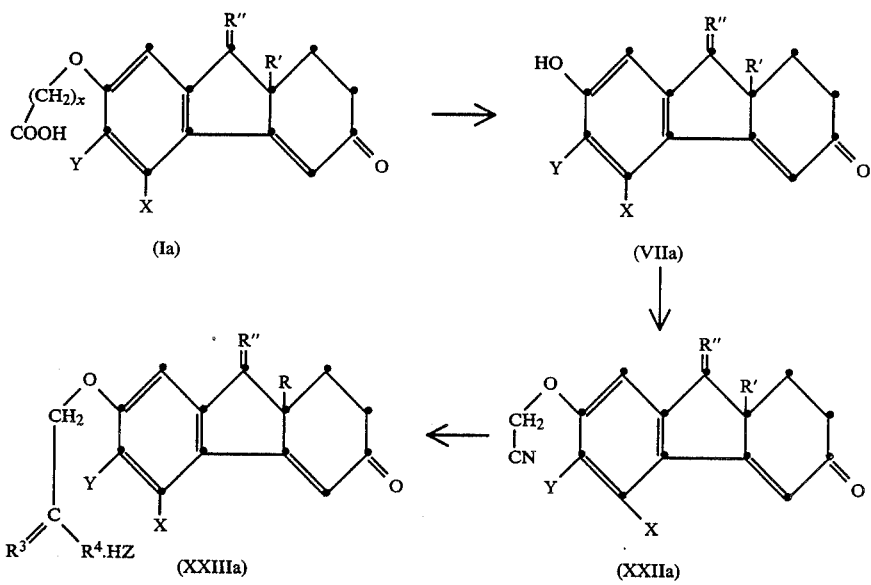

(Ia) (VIIa) (XXIIa) (XXIIIa)

The second method for producing alkanimidamides is illustrated by the 3-step synthesis of Compound XXIII

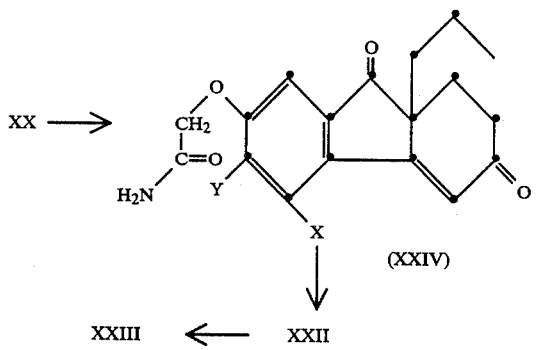

XX → (XXIV)

XXIII ← XXII from Compound XX. Reaction of Compound XX with ammonia in tetrahydrofuran or N,N-dimethylformamide at 15°–35° C. for 30 minutes to 6 hours gives amide XXIV. Reaction of Compound XXIV with N,N'dicyclohexylcarbodiimide in pyridine at 10°–25° for 20 to 45 minutes followed by stirring at ambient temperatures for 2 to 4 hours gives pure nitrile (XXII) which is converted to the pure enantiomeric ethanimidamide (XXIII) as described above. The advantage of this method, like that of the first method, is that the pure enantiomer of Compound XX (i.e. XXa) can be employed giving rise to the corresponding pure enantiomeric nitrile (XXIIa) and finally the pure enantiomer alkanimidamide (XXIIIa).

When the R'' substituent of the compounds of Formula I are other than =O, i.e. H plus a second group, both the 9- and 9a-carbon atoms are asymmetric. Therefore, these compounds consist of two diasteriomers, each composed of a racemate. The diasteriomers may be separated by well-known methods, such as fractional crystallization, column chromatography or high pressure liquid chromatography. Each racemate, then, may be resolved as described below to give the two enantiomers.

When the R'' substituent of the compounds of Formula I is =O, then only the 9a-carbon is asymmetric.

Thus, with these compounds only one racemate is possible which can be separated into its 2 enantiomers by the methods described below.

The resolution of the racemates of the compounds of Formula I of this invention where R=COOH to the corresponding two enantiomers may be accomplished by forming a salt of the racemic mixture with an optically active base such as (+) or (−) amphetamine, (−) cinchonidine, dehydroabietylamine, (+) or (−)-α-methylbenzylamine, (+) or (−)-α-(1-naphthyl)ethylamine, (+) cinchonine, brucine. or strychnine and the like in a suitable solvent such as methanol, ethanol, 2-propanol, benzene, acetonitrile, nitromethane, acetone and the like. There is formed in the solution two diastereomeric salts one of which is usually less soluble in the solvent than the other. Repetitive recrystallization of the crystalline salt generally affords a pure diastereomeric salt from which is obtained the desired pure enantiomer. The optically pure enantiomer is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

Since the carboxylic acids of Formula I of the invention are acidic, the invention also includes the obvious pharmaceutically acceptable salts, such as the sodium, potassium, ammonium, trimethylammonium, piperazinium, 1-methylpiperazinium, guanidinium, bis-(2-hydroxethyl)ammonium, N-methylglucosammonium and the like salts.

Since the alkanimidamides of Formula I of the invention are specific salts of a base, other salts, particularly the pharmaceutically acceptable ones, such as the hydrobromide, the sulfate, the methanesulfonate, the isethionate, the succinate, the maleate and the like constitute a part of this invention. These salts can be made by substituting the corresponding ammonium salt in place of ammonium chloride (which produces the hydrochloride salt). Alternatively, the salts alkanimidamides may be converted to the free base with a base much as sodium hydroxide followed by treatment with the desired acid to obtain the desired salt.

The preferred synthesis of the pure enantiomers of the alkanimidamides of this invention is to initiate the synthesis with the enantiomerically pure phenol of Formula VIIa or nitrile of Formula XXIIa. Alternatively, the resolution of the racemic alkanimides of Formula I may be accomplished by forming a salt of the racemic mixture with an optically active acid such as (+) and (−)-malic acid, (+) and (−)-dibenzoyltartariC acid, (+) and (−)-α-methoxy-α-(trifluoromethyl)phenylacetic acid, (+) and (−)-tartaric acid, d- and 1-10-camphorsulfonic acid, d- and 1-α-bromo-camphor-8-sulfonic acid and the like in a suitable solvent such as methanol, ethanol, 2-propanol, benzene, acetonitrile, nitromethane, acetone and the like. There is formed in the solution, two diastereomeric salts, one of which is usually less soluble in the solvent than the other. Repetitive recrystallization of the crystalline salt generally affords a pure diastereomeric salt form which is obtained the desired pure enantiomer. The optically pure enantiomer of the compound of Formula I is obtained by reaction of the salt with a base, isolation by filtration and recrystallization of the optically pure antipode.

The other optically pure antipode may generally be obtained by using a different acid to form the diastereomeric salt. It is of advantage to isolate the partially resolved base from the filtrates of the purification resolved base from the filtrates of the purification of the first diastereomeric salt and to further purify this substance through the use of another optically active acid. It is especially advantageous to use an optically active acid for the isolation of the second enantiomer which is the antipode of the acid used for the isolation of the first enantiomer. For example, if (−)-malic acid was used first, then (+)-malic acid is used for the isolation of the second (remaining) enantiomer.

The acid addition salts of the alkanimidamides are prepared by reacting the free bases of Formula I with an appropriate acid, for example, aqueous mineral acids, carboxylic acids or other organic acids, such as hydrochloric acid, sulfuric acid, isethionic acid, methanesulfonic acid, acetic acid and the like. If the compound is already in the form of a salt and a different salt is desired the initial salt may be reacted with a base such as sodium hydroxide to generate the free base which in turn may be reacted with another acid to form a new salt.

The reaction may be conducted in water but it is preferred to conduct the reaction in an organic solvent, such as ether, ethanol, N,N-dimethylformamide and the like.

The preferred salts are the pharmaceutically acceptable salts such as the hydrochloride salts and the like.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions and elevated intracranial pressure, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 20 mg/kg of body weight as a single dose, preferably from 0.5 mg/kg to 10 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 4, 6 and 8 mg/kg of body weight can be given at 6 hour intervals. If necessary, 4 additional doses of 8 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, presevatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. August 29–31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^+$ and/or release of neurotransmitters, edema, hypoxia and necrosis. Astroglial swelling results directly from a $K^+$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R. ; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, c.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V. ; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention can be tested for activity. This test provides the principal in vitro evaluation and consists of a determination of concentration vs. response curve. The addition of $HCO_3^-$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulates statistically significant and comparable increases in cerebrocortical tissue swelling and ion levels. After addition of drug to the incubation media, detailed drug concentration-response curves are then obtained. The data are expressed as percent $HCO_3^-$-stimulated swelling vs. drug concentration, from which the concentration of drug providing 50% inhibition of $HCO_3^-$-stimulated swelling ($I_{50}$ in molarity) is interpolated.

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims. All temperatures in the examples are in Centigrade unless otherwise indicated.

EXAMPLE 1

In Vitro Cerebrocortical Tissue Slice Assay

Adult cats of 2–3 kg body weight are employed in tissue slice studies. Prior to sacrifice, the animals are anesthetized with ketamine hydrochloride (Ketaset), 10 mg/kg intramuscularly. Eight (three control, five experimental) pial surface cerebrocortical tissue slices (0.5-mm thick; approximately 150 mg initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed, in an individual Warburg flask containing 2 ml of incubation medium at room temperature. The basic composition of the incubation media, in millimoles per liter, is as follows: glucose, 10; $CaCl_2$, 1.3; $MgSO_4$, 1.2; $KHSO_4$, 1.2; Hepes (N-2-hydroxyethylpiperazine-N'-2-ethanesulfonic acid, titrated with NaOH to pH 7.4), 20. Except when adding $HCO_3^-$, the osmolarity of the media is maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, $NaHCO_3$ or triethylammonium bicarbonate (TEAB) is initially present in the sidearm of each flask at an initial concentration of 50 mM in 0.5 ml of complete medium. Nonbicarbonate control slices are incubated at 37° C. in 2.5 ml of basic medium for 60 minutes. Bicarbonate control slices are similarly incubated for an initial 20 minutes at 37° C. in 2.0 ml of basic medium to which is added from the sidearm an additional 0.5 ml of incubation medium containing 50 mM $HCO_3^-$, which, after mixing, results in a $HCO_3^-$ concentration of 10 mM and a total volume of 2.5 ml. The incubation is continued for an additional 40 minutes. The various compounds to be tested are dissolved by forming the hydrochloride salts in water. When only the free bases are available, the hydrochloride salts are formed by treating the free base with a molar equivalent of hydrochloric acid and diluting to the appropriate concentrations. Just prior to incubation, all flasks containing $HCO_3^-$ are gassed for 5 minutes with 2.5% $CO_2$/97.5% $O_2$ instead of 100% $O_2$.

Following the 60-minute incubation period, tissue slices are separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration is measured by the amount of $HCO_3^-$-stimulated swelling that occurred in its presence, computed as a percent of the maximum possible. Tissue and media $Na^+$ and $K^+$ levels are determined by emission flame photometry with $Li^+$ internal standard; $Cl^-$ levels are determined by amperometric titration. Tissue viability during incubation is monitored by manometry.

EXAMPLE 2

[(5,6-Dichloro-3,9-dioxo-9a-propyl2,3,9,9a-tetrahydro-1H-fluoren-7-yl)oxy]acetic Acid

Step A:
9-Bromo-5,6-dichloro-7-methoxy-9a-propyl-1,2,9,9a-tetrahydro-3H-fluoren-3-one A mixture of 5,6-dichloro-1,2,9,9a-tetrahydro-7-methoxy-9a-propyl-3H-fluoren-3-one (3.25 g, 0.01 mol), N-bromosuccinimide (1.78 g, 0.01 mole) and benzoyl peroxide (75 mg) in carbon tetrachloride (50 ml) was heated at reflux for 1¾ hours, cooled, filtered and the $CCl_4$ distilled at reduced pressure to give 3.70 g 9-bromo-5,6-dichloro-7-methoxy-9a-propyl-1,2,9,9a-tetrahydro-3H-fluoren-3-one which melted at 131.5°–133.5° C. after crystallization from diethyl ether.

Analysis for $C_{17}H_{17}BrCl_2O_2$: Calc'd: C, 50.52; H, 4.24. Found: C, 50.61; H, 4.30.

Step B:
5,6-Dichloro-9-hydroxy-7-methoxy-9a-propyl-1,2,9,9a-tetrahydro-3H-fluoren-3-one A mixture of 9-bromo-5,6-dichloro-7-methoxy-9a-propyl-1,2,9,9a-tetrahydro-3H-fluoren-3-one (6.29 g, 0.0157 mole) and silver nitrate (7.89 g, 0.047 mol) in 2-methoxyethanol (200 ml) and $H_2O$ (100 ml) was heated at reflux for 2 hours, filtered and evaporated to dryness. Chromatography of the residue on silica gel eluted with ethyl acetate-hexane (1:1) gave 1.2 g of 5,6-dichloro-9-hydroxy-7-methoxy-9a-propyl-1,2,9,9a-tetrahydro-3H-fluoren-3-one which melted at 173°–5° C. and was used in Step C without further purification.

Step C:
5,6-Dichloro-7-methoxy-9a-propyl-1,2,9,9a-tetrahydro-3H-fluoren-3,9-dione To a solution of 5,6-dichloro-9-hydroxy-7-methoxy-9a-propyl-1,2,9,9a-tetrahydro-3H-fluoren-3-one (3.03 g, 0.089 mol) in a mixture of acetone (75 ml), ether (75 ml) and water (7 ml) cooled to 5° C. was added Jones reagent (3.4 ml, 2.67N). The reaction mixture was stirred for ¼ hour at 5° C. then for 1½ hours at 25° C. The reaction mixture was diluted with ether and $H_2O$, the ether layer washed with $NaHCO_3$, dried over $MgSO_4$, evaporated and chromatographed on silica gel eluting with ethyl acetate-hexane (1:1.5) to give 5,6-dichloro-7-methoxy-9a-propyl-1,2,9,9a-tetrahydro-3H-fluoren-3,9-dione which melts at 167°–9° C.

Analysis for $C_{17}H_{16}Cl_2O_3$: Calc'd: C, 60.19; H, 4.75. Found: C, 60.21; H, 4.87.

Step D:
5,6-Dichloro-7-hydroxy-9a-propyl-1,2,9,9a-tetrahydro-3H-fluoren-3,9-dione A mixture of 5,6-dichloro-7-methoxy-9a-propyl-1,2,9,9a-tetrahydro-3H-fluoren-3,9-dione (2.67 g) and pyridine hydrochloride (35 g) was heated at 175°–180° C. in an inert atmosphere for ¾ hour, poured into ice water and extracted with a mixture of ether and tetrahydrofuran. The organic extracts were washed with water, dried over $MgSO_4$ and evaporated in vacuo to give 5,6-dichloro-7-hydroxy-9a-propyl-1,2,9,9a-tetrahydro- 3H-fluoren-3,9-dione which was used in Step E without further purification.

Step E:
[5,6-Dichloro-3,9-dioxo-9a-propyl-2,3,9,9a-tetrahydro-1H-fluoren-7-yl)oxy]acetic acid A stirred mixture of 5,6-dichloro-7-hydroxy-9a-propyl-1,2,9,9a-tetrahydro-3H-fluoren-3,9-dione (2.3 g, 0.0071 mol) ethyl bromoacetate (2.36 g, 0.014 mole) and potassium carbonate (1.38 g, 0.01 mol) in N,N-dimethylformamide (30 ml) was heated at 60°–65° C. for 4 hours, poured into ice water, extracted into a mixture of ether and tetrahydrofuran (3:1), washed with water, dried over MgSO4 and evaporated in vacuo. The crude ester thus obtained was purified by chromatography on silica gel eluting with methylene chloride-ethyl acetate (25:1). The ester was hydrolysed by stirring in a mixture of ethanol (50 ml) and 1N sodium hydroxide (6 ml) for 3 hours. Dilution with water and acidification with hydrochloric acid gave [5,6-dichloro-3,9-dioxo-9a-propyl-2,3,9,9a-tetrahydro-1H-fluoren-7-yl)oxy]acetic acid as a yellow solid, m.p.=292°–4° C.

Analysis for $C_{18}H_{16}Cl_2O_5$: Calc'd: C, 56.41; H, 4.21. Found: C, 56.15; H, 4.37.

EXAMPLE 3

Resolution of [(5,6-Dichloro-3,9-dioxo-9a-propyl-2,3,9,9a-tetrahydro-1H-fluoren-7-yl)oxy]acetic acid Racemic [(5,6-dichloro-3,9-dioxo-9a-propyl-2,3,9,9a-tetrahydro-1H-fluoren-7-yl)oxy]acetic acid (3.82 g, 10 mMole) in acetonitrile (270 ml) is heated to boiling and cinchonine (2.95 g, 10 mmol) was added. The solution was stirred at 5° C. for 24 hours and the solid that separated was filtered off, washed with aceto and the filtrate was (I) saved. The salt was recrystallized from acetonitrile and the product removed by filtration, dried, treated with 1 normal hydrochloric acid (50 mL) and extracted with 20% tetrahydrofuran in ether to give the pure enantiomer. The extract was dried over MgSO4; the solvent was evaporated in vacuo and the residue recrystallized to give the pure enantiomer of [(5,6-dichloro-3,9-dioxo-9a-propyl-2,3,9,9a-tetrahydro-1H-fluoren-7-yl)oxy]acetic acid.

Filtrate (I) was evaporated in vacuo, treated with 2 normal hydrochloric acid (45 mL), extracted with 20% tetrahydrofuran in ether and the extract was dried over MgSO4. The solvent was evaporated in vacuo and the residue dissolved in acetonitrile (250 mL), heated to boiling and cinchonidine (2.95 g, 10 mmol) was added. The solution was cooled to 5° C. and stirred for 24 hours. The solid that separated was recrystallized and worked up as described above for the other (opposite) enantiomer of [(5,6-dichloro-3,9-dioxo-9a-propyl-2,3,9,9a-tetrahydro-1H-fluoren-7-yl)oxy]acetic acid.

EXAMPLE 4

[(5,6-Dichloro-9-hydroxy-3-oxo-9a(R)-propyl-2,3,9,9a-tetrahydro-1H-fluoren-7-yl)oxy]acetic acid.

Step A: Ethyl R(+)[(5,6-dichloro-3-oxo-9a-propyl-2,3,9,9a-tetrahydro-1H-fluoren-7-yl)oxy]acetate A mixture of R(+)[(5,6-dichloro-3-oxo-9a-propyl-2,3,9,9a-tetrahydro-1H-fluoren-7-yl)oxy]acetic acid (10.7 g, 0.029 mole), concentrated sulfuric acid (1 ml) and ethanol (100 ml) was refluxed for 2 hours, cooled, diluted with water and extracted into ether and methylene chloride. The organic extracts were washed with sodium bicarbonate, water, dried over MgSO4 and evaporated at reduced pressure. Trituration with hexane gave 10.85 g of ethyl R(+)[(5,6-dichloro-3-oxo-9a-propyl-2,3,9,9a-tetrahydro-1H-fluoren-7-yl)oxy]acetate which melted at 106.5°–108.5° C.

Step B: Ethyl [(9-Bromo-5,6-dichloro-3-oxo-9a(R)-propyl-2,3,9,9a-tetrahydro-1H-fluoren-7-yl)oxy]acetate A stirred mixture of ethyl R(+)[(5,6-dichloro-3-oxo-9a-propyl-2,3,9,9a-tetrahydro-1H-fluoren-7-yl)oxy]acetate (7.95 g, 0.02 mol), N-bromosuccinimide (3.58 g, 0.02 mol) and benzoyl peroxide (90 mg) in carbon tetrachloride (90 ml) was heated at reflux for 2 hours, filtered, evaporated at reduced pressure then chromatographed on silica gel eluting with ethyl acetate-hexane (1:3) to give ethyl [(9-bromo-5,6-dichloro-3-oxo-9a(R)-propyl-2,3,9,9a-tetrahydro-1H-fluoren-7-yl)oxy]acetate which was used in Step C without further purification.

Step C: Ethyl [(9-Acetoxy-5,6-dichloro-3-oxo-9a(R)-propyl-2,3,9,9a-tetrahydro-1H-fluoren-7-yl)oxy]acetate A stirred mixture of ethyl [(9-acetoxy-5,6-dichloro-3-oxo-9a(R)-propyl-2,3,9,9a-tetrahydro-1H-fluoren-7-yl)oxy]acetate (8.2 g, 0.017 mol), silver acetate (6.32 g, 0.038 mol), water (0.75 ml) and acetic acid (75 ml) was heated at 100° C. for 3 hours, filtered and the acetic acid distilled at reduced pressure. The residue was dissolved in ether, washed with water, dried over MgSO4, evaporated in vacuo and chromatographed on silica gel to give ethyl [(9-acetoxy-5,6-dichloro-3-oxo-9a(R)-propyl-2,3,9,9a-tetrahydro-1H-fluoren-7-yl)oxy]acetate which melted at 128.5°–130.5° C.

Analysis for $C_{22}H_{24}Cl_2O_6$: Calc'd: C, 58.03; H, 5.31. Found: C, 58.37; H, 5.40.

Step D:
[(5,6-Dichloro-9-hydroxy-3-oxo-9a(R)-propyl-2,3,9,9a-tetrahydro-1H-fluoren-7-yl)oxy]acetic acid A mixture of ethyl [(9-acetoxy-5,6-dichloro-3-oxo-9a(R)-propyl-2,3,9,9a-tetrahydro-1H-fluoren-7-yl)oxy]acetate (4.27 g, 0.0094 mol), methanol (75 ml) and 1N sodium hydroxide (21 ml) was stirred at 25° C. for 4 hours, diluted with water (250 ml), acidified with HCl and extracted with ether and methylene chloride. The combined organic extracts were combined, washed with H2O, dried over MgSO4 and evaporated in vacuo to give [(5,6-dichloro-9-hydroxy-3-oxo-9a(R)-propyl-2,3,9,9a-tetrahydro-1H-fluoren-7-yl)oxy]acetic acid which melted at 206°–208° C.

Analysis for $C_{18}H_{18}Cl_2O_5$: Calc'd: C, 56.12; H, 4.71. Found: C, 56.42; H, 4.79.

EXAMPLE 5

[(5,6-Dichloro-9a-ethyl-9-methyl-3-oxo-2,3,9,9a-tetrahydro-1H-fluoren-7-yl)oxy]acetic acid Step A: Methyl [(6,7-Dichloro-2-ethyl-2,3-dihydro-3-methyl-1-oxo-2-(3-oxobutyl)-1H-inden-5-yl)oxy]acetate To a solution of methyl [(6,7-dichloro-2-ethyl-2,3-dihydro-3-methyl-1-oxo-1H-inden-5-yl)oxy]acetate (0.8 g) in tetrahydrofuran (7.5 ml) was added methyl vinyl ketone (0.45 ml) and 1,5-diazabicyclo[4.3.0]non-5-ene (DBN) (75 μl). The reaction mixture was heated at 60° C. for five hours during which time DBN (2×75 μl)

was added. The reaction mixture was poured into ice water, extracted with ether, washed with water, dried over MgSO₄ and evaporated in vacuo. Chromatography on silica gel eluting with ethyl acetate-hexane (1:1) gave methyl [(6,7-dichloro-2-ethyl-2,3-dihydro-3-methyl-1-oxo-2-(3-oxobutyl)-1H-inden-5-yl)oxy]acetate which was used in Step B without further purification.

Step B:
[(5,6-Dichloro-9a-ethyl-9-methyl-3-oxo-2,3,9,9a-tetrahydro-1H-fluoren-7-yl)oxy]acetic acid A solution of methyl [(6,7-dichloro-2-ethyl-2,3-dihydro-3-methyl-1-oxo-2-(3-oxobutyl)-1H-inden-5-yl)oxy]acetate (0.40 g) in acetic acid (6 ml) and 6N hydrochloric acid (6 ml) was heated at reflux for 90 hours, poured into ice water, extracted into ether, washed with water, brine, dried over MgSO₄ and evaporated in vacuo. Crystallization from butyl chloride gave [(5,6-dichloro-9a-ethyl-9-methyl-3-oxo-2,3,9,9a-tetrahydro-1H-fluoren-7-yl)oxy]acetic acid which melted at 212°–214° C.

Analysis for $C_{18}H_{18}Cl_2O_4$: Calc'd: C, 58.55; H, 4.91. Found: C, 58.78; H, 5.10.

EXAMPLE 6
[(9-Amino-5,6-dichloro-3-oxo-9a(R)-propyl-2,3,9,9a-tetrahydro-1H-fluoren-7-yl)oxy]acetic acid

Step A: Ethyl [9-Azido-5,6-dichloro-3-oxo-9a(R)-propyl-2,3,9,9a-tetrahydro-1H-fluoren-7-yl)oxy]acetate A stirred mixture of ethyl [(9-bromo-5,6-dichloro-3-oxo-9a(R)-propyl-2,3,9,9a-tetrahydro-1H-fluoren-7-yl)oxy]acetate (Example 4, Step B) (5.1 g, 0.0107 mole), sodium azide (1.39 g, 0.021 mol), tetrabutylammonium bromide (0.345 g, 0.00107 mol), benzene (45 ml) and N,N-dimethylformamide (20 ml) was heated at reflux for 39 hours, diluted with H₂O and extracted with ether. The organic extracts were washed with water, dried over MgSO₄, evaporated in vacuo and the residue chromatographed on silica gel eluted with ethyl acetate-hexane (1:3.5) to give ethyl [9-azido-5,6-dichloro-3-oxo-9a(R)-propyl-2,3,9,9a-tetrahydro-1H-fluoren-7-yl)oxy]acetate which was used in Step B without further purification.

Step B: Ethyl [(9-Amino-5,6-dichloro-3-oxo-9a(R)-propyl-2,3,9,9a-tetrahydro-1H-fluoren-7-yl)oxy]acetate hydrochloride A solution of ethyl [(9-azido-5,6-dichloro-3-oxo-9a(R)-propyl-2,3,9,9a-tetrahydro-1H-fluoren-7-yl)oxy]acetate (2.229 g, 0.00517 mole) and triphenylphosphine (1.493 g, 0.00569 mole) in tetrahydrofuran (30 ml) was refluxed with stirring for 4 hours. Then, water (0.4 ml) was added and refluxing was continued for another 16 hours. After cooling and evaporating the solvents in vacuo, the residue was dissolved in ether, dried over sodium sulfate, filtered and the filtrate acidified with ethanolic hydrogen chloride. The solid that separated was removed by filtration, washed with hot ethanol and dried. The ethyl [(9-amino-5,6-dichloro-3-oxo-9a(R)-propyl-2,3,9,9a-tetrahydro-1H-fluoren-7-yl)oxy]acetate hydrochloride weighed 940 mg; m.p. 261° C.(d).

Anal. Calc'd for $C_{20}H_{23}Cl_2NO_4 \cdot HCl$: Calc'd: C, 53.52; H, 5.39; N, 3.12; Cl, 23.70. Found: C, 53.44; H, 5.52; N, 2.90; Cl, 23.45.

Step C:
[(9-Amino-5,6-dichloro-3-oxo-9a(R)-propyl-2,3,9,9a-tetrahydro-1H-fluoren-7-yl)oxy]acetic acid Ethyl [(9-amino-5,6-dichloro-3-oxo-9a(R)-propyl-2,3,9,9a-tetrahydro-1H-fluoren-7-yl)oxy]acetate hydrochloride (497.5 mg, 0.002 mole) is dissolved in a mixture of ethanol (17 ml), water (3 ml) and 1N sodium hydroxide (5 ml). The mixture is stirred at 25° C. for 10 hours, evaporated to dryness in vacuo and the residue dissolved in water (20 ml) and carefully neutralized with hydrochloric acid to the isoelectric points whereby a precipitate separates. The product is removed by filtration, washed with water and dried to give [(9-amino-5,6-dichloro-3-oxo-9a(R)-propyl-2,3,9,9a-tetrahydro-1H-fluoren-7-yl)oxy]acetic acid.

EXAMPLE 7
{[5,6-Dichloro-9-(diethoxyphosphoramido)-3-oxo-9a(R)-propyl-2,3,9,9a-tetrahydro-1H-fluoren-7-yl]oxy}acetic acid A solution of triethylphosphite (0.75 ml, 3.62 mmol) in benzene (10 ml) was added at 25° C. over a 5 minute period to a stirred solution of ethyl [(9 azido-5,6-dichloro-3-oxo-9a(R)-propyl-2,3,9,9a-tetrahydro-1H-fluoren-7-yl)oxy]acetate (Example 6, Step A) (1.5 g, 3.42 mmol) in benzene (25 ml). After stirring at 25° C. for 18 hours, the reaction mixture was saturated with dry HCl, evaporated at reduced pressure and dissolved in 0.5N sodium hydroxide (30 ml). The basic solution was acidified with hydrochloric acid and the {([5,6-dichloro-9-(diethoxyphosphoramido)-3-oxo-9a(R)-propyl-2,3,9,9a-tetrahydro-1H-fluoren-7-yl]oxy}acetic acid which separated was filtered, washed with water and ether and dried; m.p. 217°–222° C.

Analysis Calc'd for $C_{22}H_{28}Cl_2NO_7P$: Calc'd: C, 50.78; H, 5.42; N, 2.69; P, 5.95. Found: C, 51.19; H, 5.43; N, 2.64; P, 5.73.

EXAMPLE 8
1-Carboxy-1-methylethyl [(5,6-Dichloro-3,9-dioxo-9a-propyl-2,3,9,9a-tetrahydro-1H-fluoren-7-yl)oxy]acetate

[(5,6-Dichloro-3,6-dioxo-9a-propyl-2,3,9,9a-tetrahydro-1H-fluoren-7-yl)oxy]acetic acid (3.83 g, 10 mmole) is dissolved in tetrahydrofuran (20 ml). 1,1-Carbonyldiimidazole (3.2 g, 10 mmole) is added and the mixture stirred at 20° C. for one hour. 2-Hydroxy-2-methylpropionic acid (1.05 g, 10 mmole) is added and the mixture stirred for 18 hours at 25° C. The solvent is removed by evaporation in vacuo and the residue dissolved in methylene chloride, washed with water and dried over magnesium sulfate. The solvent is removed by evaporation in vacuo and the residue purified by column chromatography over silica (250 g) using a methylene chloride/tetrahydrofuran/acetic acid 100/2/1 (v/v/v) mixture as the eluant. Selecting the appropriate fractions gave 1-carboxy-1-methylethyl [(5,6-Dichloro-3,9-dioxo-9a-propyl-2,3,9,9a-tetrahydro-1H-fluoren-7-yl)oxy]acetate upon evaporation of the solvent.

EXAMPLE 9
2-[(5,6-Dichloro-3,9-dioxo-9a-propyl-1H-fluoren-7-yl)oxy]ethanimidamide hydrochloride Step A: [(5,6-Dichloro-3,9-dioxo-9a-propyl-2,3,9,9a-tetrahydro-1H-fluoren-7-yl)oxy]acetamide

[(5,6-Dichloro-3,9-dioxo-9a-propyl-2,3,9,9a-tetrahydro-1H-fluoren-7-yl)oxy]acetic acid (3.82 g, 10 mMole) is dissolved in tetrahydrofuran (30 ml) and 1,1-carbonyldiimidazole (1.78 g, 11 mMole) and the mixture stirred at ambient temperature for 30 minutes. The solution is saturated with ammonia gas and then stirred at ambient temperature for 24 hours and at 50° for 16 hours. Evaporation of the solvent and addition of water yields [(5,6-dichloro-3,9-dioxo-9a-propyl-2,3,9,9a-tetrahydro-1H-fluoren-7-yl)oxy]acetamide which is separated by filtration, washed with water, and dried.

Step B:
[(5,6-Dichloro-3,9-dioxo-9a-propyl-2,3,9,9a-tetrahydro-1H-fluoren-7-yl)oxy]acetonitrile

[(5,6-Dichloro-3,9-dioxo-9a-propyl-2,3,9,9a-tetrahydro-1H-fluoren-7-yl)oxy]acetamide (3.65 g, 10 mMole) is dissolved in pyridine (25 ml) and N,N'-dicyclohexylcarbodiimide (2.17 g, 10.5 mMole) in pyridine (15 ml) is added portionwise over 30 minutes with stirring at 15°-20° C. The mixture is then stirred at ambient temperature for 3 hours. The precipitated dicyclohexylurea is removed by filtration and the pyridine removed from the filtrate by evaporation in vacuo. Addition of water to the residue gives the product which is dissolved in methylene chloride, dried over MgSO$_4$ and the solvent removed to provide the [(5,6-dichloro-3,9-dioxo-9a-propyl-2,3,9,9a-tetrahydro-1H-fluoren-7-yl)oxy]acetonitrile.

Step C:
2-[(5,6-Dichloro-3,9-dioxo-9a-propyl-2,3,9,9a-tetrahydro-1H-fluoren-7-yl)oxy]ethanimidamide hydrochloride

[(5,6-Dichloro-3,9-dioxo-9a-propyl-2,3,9,9a-tetrahydro-1H-fluoren-7-yl)oxy]acetonitrile (3.49 g, 10 mMole), chloroform (40 ml) and ethanol (650 mg, 11 mMole) are united and saturated with hydrogen chloride gas at 0° C. The mixture is stirred for 16 hours and then basified with 10 normal sodium hydroxide solution. The chloroform layer is separated, washed with water, dried over K$_2$CO$_3$, and evaporated in vacuo. The residue is dissolved in ethanol (30 ml) and water (5 ml) added. The mixture is stirred and treated with ammonium chloride (700 mg, 12 mMole). After stirring at ambient temperature for 4 hours, the mixture is filtered, the filtrate evaporated to near dryness in vacuo, and the residue treated with acetone (50 ml). The solid that separates is removed by filtration, washed with acetone, dried, and recrystallized from a mixture of ethanol and ether to give 2-[(5,6-dichloro-3,9-dioxo-9a-propyl-2,3,9,9a-tetrahydro-1H-fluoren-7-yl)oxy]ethanimidamide hydrochloride.

By using the (+)-enantiomer of [(5,6-dichloro-3,9-dioxo-9a-propyl-2,3,9,9a-tetrahydro-1H-fluoren-7-yl)oxy]acetic acid from Example 3, in Example 9, Step A, instead of the racemate and using the product of that reaction in Step B and the product of Step B in Step B, there is obtained the (+)-enantiomer of 2-[(5,6-dichloro-3,9-dioxo-9a-propyl-2,3,9,9a-tetrahydro-1H-fluoren-7-yl)oxy]ethanimidamide hydrochloride.

Similarly, if the (−)-enantiomer from Example 3 is used in Example 9, Step A, the final product in Step C is the (−)-enantiomer of 2-[(5,6-fluoren-7-yl)oxy]ethanimidamide hydrochloride.

EXAMPLE 10

[(3-Oxo-9a(R)-propyl-2,3,9,9a-tetrahydro-5,6,9-trichloro-1H-fluoren-7-yl)oxy]acetic acid Step A: Ethyl [(3-Oxo-9a(R)-propyl-2,3,9,9a-tetrahydro-5,6,9-trichloro-1H-fluoren-7-yl)oxy]acetate A stirred mixture of ethyl R(+)[(5,6-dichloro-3-oxo-9a-propyl-2,3,9,9a-tetrahydro-1H-fluoren-7-yl)oxy]acetate (Example 4, Step A) (7.95 g, 0.02 mole), N-chlorosuccinimide (2.94 g, 0.022 mole) and benzoyl peroxide (90 mg) in carbon tetrachloride (200 ml) was refluxed for 10 hours. The solution was cooled, filtered and the solvent evaporated in vacuo. The residue was purified by column chromatography on silica gel (500 g), eluting with ethyl acetate-hexane (1:3) to give ethyl [(3-oxo-9a(R)-propyl-2,3,9,9a-tetrahydro-5,6,9-trichloro-1H-fluoren-7-yl)oxy]acetate by evaporation of the relevant fractions.

Step B:
[(3-Oxo-9a(R)-propyl-2,3,9,9a-tetrahydro-5,6,9-trichloro-1H-fluoren-7-yl)oxy]acetic acid Ethyl [(3-oxo-9a(R)-propyl-2,3,9,9a-tetrahydro-5,6,9-trichloro-1H-fluoren-7-yl)oxy]acetate (4.31 g, 0.01 mole) was stirred with ethanol (50 ml) and 1N sodium hydroxide (15 ml) for 12 hours at 25° C. The solution was evaporated in vacuo and the residue dissolved in water. Acidification with hydrochloric acid gave [(3-oxo-9a(R)-propyl-2,3,9,9a-tetrahydro-5,6,9-trichloro-1H-fluoren-7-yl)oxy]acetic acid which was purified by column chromatography on silica gel (400 g) eluting with methylene chloride/tetrahydrofuran/acetic acid, 50/2/1 (v/v/v).

EXAMPLE 11

Parenteral Solution of the Sodium Salt of [(5,6-Dichloro-3,9-dioxo-9a-propyl-2,3,9,9a-tetrahydro-1H-fluoren-7-yl)oxy]acetic acid The [(5,6-dichloro-3,9-dioxo-9a-propyl-2,3,9,9a-tetrahydro-1H-fluoren-7-yl)oxy]acetic acid (Example 2, Step E) (500 mg) is dissolved by stirring and warming with a solution of 0.25N sodium bicarbonate (5.6 ml). The solution is diluted to 10 ml with water and sterilized by filtration. All the water that is used in the preparation is pyrogen-free. The concentration of the active ingredient (calculated as free acid) in the final solution is 5%.

EXAMPLE 12

Parenteral Solution of the Sodium Salt of [(5,6-Dichloro-9-hydroxy-3-oxo-9a(R)-propyl-2,3,9,9a-tetrahydro-1H-fluoren-7-yl)oxy]acetic acid The [(5,6-dichloro-9-hydroxy-3-oxo-9a(R)-propyl-2,3,9,9a-tetrahydro-1H-fluoren-7-yl)oxy]acetic acid (Example 4, Step D) (500 mg) is dissolved by stirring and warming with a solution of 0.25N sodium bicarbonate (5.6 ml). The solution is diluted to 10 ml with water and sterilized by filtration. All the water that is used in the preparation is pyrogen-free. The concentration of the active ingredient (calculated as free acid) in the final solution is 5%.

Similar parenteral solutions of the carboxylic acids of this invention can be prepared by replacing the active ingredient of this Example by any of the other carboxylic acids of this invention.

EXAMPLE 13

Parenteral Solution of 2-[(5,6-Dichloro-3,9-dioxo-9a-propyl-1H-fluoren-7-yl)oxy]ethanimidamide hydrochloride 2-[(5,6-Dichloro-3,9-dioxo-9a-propyl-1H-fluoren-7-yl)oxy]ethanimidamide hydrochloride (Example 9, Step C) (546 mg) is dissolved by stirring and warming with sufficient water to make a total volume of 10 ml. The solution is diluted to 10 ml with water and sterilized by filtration. All the water that is used in the preparation is pyrogen-free. The concentration of the active ingredient (calculated as free base) in the final solution is 5%.

Similar parenteral solutions of the alkanimidamide salts of this invention can be prepared by replacing the active ingredient of this Example by any of the other alkanimidamide salts of this invention.

EXAMPLE 14

Dry-Filled Capsules Containing 100 mg of Active Ingredient (Free Acid) Per Capsule

|  | Per Capsule |
|---|---|
| 1-Carboxy-1-methylethyl [(5,6-dichloro-3,6-dioxo-9a-propyl-2,3,9,9a-tetrahydro-1H—fluoren-7-yl)oxy]acetate | 100 mg |
| Lactose | 99 mg |
| Magnesium Stearate | 1 mg |
| Capsule (Size No. 1) | 200 mg |

The 1-carboxy-1-methylethyl [(5,6-dichloro-3,6-dioxo-9a-propyl-2,3,9,9a-tetrahydro-1H-fluoren-7yl)oxy]acetate (Example 8) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules of the compounds of this invention which are not salts can be prepared by replacing the active ingredient of this Example by any of the other non-salts of this invention.

EXAMPLE 15

Dry-Filled Capsules Containing 100 mg of Active Ingredient (Free Base) Per Capsule

|  | Per Capsule |
|---|---|
| Ethyl [(9-amino-5,6-dichloro-3-oxo-9a(R)—propyl-2,3,9,9a-tetrahydro-1H—fluoren-7-yl)oxy]acetate hydrochloride | 109 mg |
| Lactose | 90 mg |
| Magnesium Stearate | 1 mg |
| Capsule (Size No. 1) | 200 mg |

The ethyl [(9-amino-5,6-dichloro-3-oxo-9a(R)-propyl-2,3,9,9a-tetrahydro-1H-fluoren-7-yl)oxy]acetate hydrochloride (Example 6, Step B) is reduced to a No. 0 powder and then the lactose and magnesium stearate are passed through a No. 60 bolting cloth onto the powder and the combined ingredients admixed for 10 minutes and then filled into a No. 1 dry gelatin capsule.

Similar capsules of the salts of this invention can be prepared by replacing the active ingredient of this Example by any of the other salts of this invention.

What is claimed is:

1. A compound of the formula:

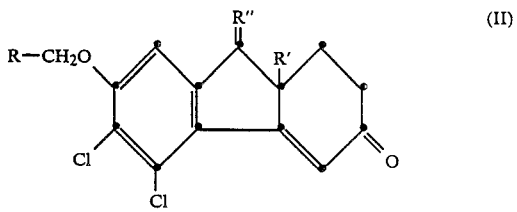

wherein:
R is

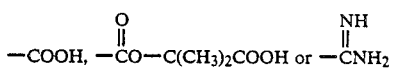

R' is lower alkyl, branched or unbranched, containing from 1 to 5 carbon atoms; and
R" is =O, H plus

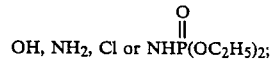

and the pharmaceutically acceptable salts thereof.

2. A compound according to claim 1, which is [(5,6-dichloro-3,9-dioxo-9a-propyl-2,3,9,9a-tetrahydro-1H-fluoren-7-yl)oxy]acetic acid.

3. A compound according to claim 2, which is the (+)-enantiomer.

4. A compound according to claim 2, which is the (−)-enantiomer.

5. A compound of claim 1, which is 1-carboxy-1-methylethyl [(5,6-dichloro-3,9-dioxo-9a-propyl-2,3,9,9a-tetrahydro-1H-fluoren-7-yl)oxy]acetate.

6. A compound of claim 5, which is the (+)-enantiomer.

7. A compound of claim 5, which is the (−)-enantiomer.

8. A compound of claim 1, which is [(5,6-dichloro-9-hydroxy-3-oxo-9a(R)-propyl-2,3,9,9a-tetrahydro-1H-fluoren-7-yl)oxy]acetic acid.

9. A compound of claim 1, which is ethyl [(9-amino-5,6-dichloro-3-oxo-9a(R)-propyl-2,3,9,9a-tetrahydro-1H-fluoren-7-yl)oxy]acetate hydrochloride.

10. A compound of claim 1, which is [(3-oxo-9a(R)-propyl-2,3,9,9a-tetrahydro-5,6,9-trichloro-1H-fluoren-7-yl)oxy]acetic acid.

11. A compound of claim 1, which is {[(5,6-dichloro-9-(diethoxyphosphoramido)-3-oxo-9a(R)-propyl-2,3,9,9a-tetrahydro-1H-fluoren-7-yl]oxy}acetic acid.

12. A compound of claim 1, which is 2-[(5,6-dichloro-3,9-dioxo-9a-propyl-2,3,9,9a-tetrahydro-1H-fluoren-7-yl)oxy]ethanimide amide hydrochloride.

13. A compound of claim 12, which is the (+)-enantiomer.

14. A compound of claim 12, which is the (−)-enantiomer.

15. A pharmaceutical compostion useful in the treatment of grey matter edema comprising a pharmaceutical carrier and an effective amount of a compound of claim 1.

16. A method of treating a person with grey matter edema which comprises administering to such a person an effective amount of a compound of claim 1.

* * * * *